Sept. 22, 1964 R. G. JELLY Plant Pat. 2,446
ROSE PLANT
Filed Oct. 21, 1963
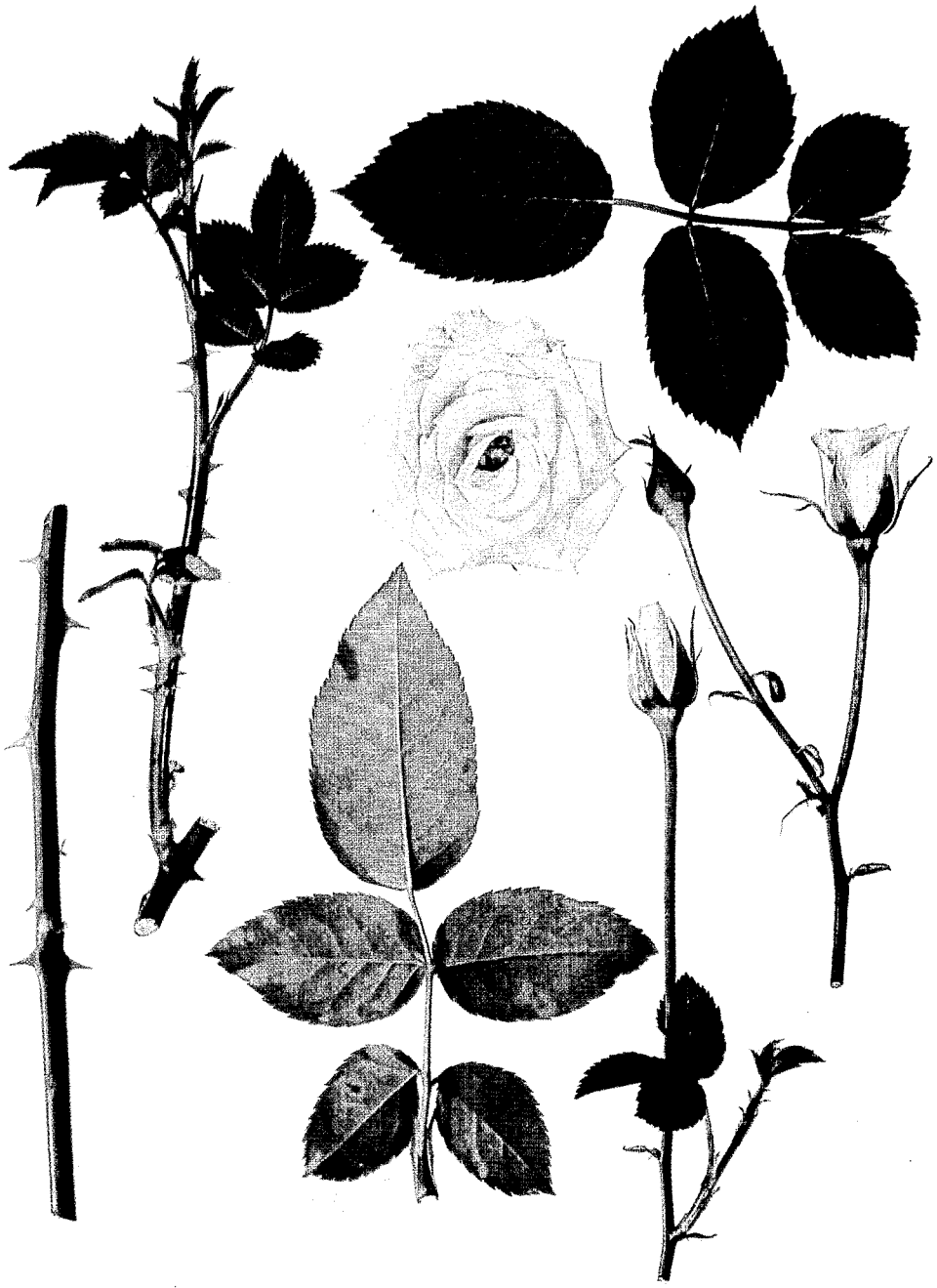
Inventor.
Robert G. Jelly
By: Robb & Robb
Attorneys.

United States Patent Office

Plant Pat. 2,446
Patented Sept. 22, 1964

2,446
ROSE PLANT

Robert G. Jelly, Richmond, Ind., assignor to E. G. Hill Co., Inc., Richmond, Ind., a corporation of Indiana Filed Oct. 21, 1963, Ser. No. 317,858
1 Claim. (Cl. Plt.—26)

The present invention relates to a new and distinct variety of rose plant of the floribunda class, which was originated by me by crossing the variety "Stoplite" (Plant Patent No. 1315) with the variety "Lovelight" (Plant Patent No. 1887).

The primary objective of this breeding was to produce an improved rose variety in the class of medium shade pink floribundas grown commercially as cut flowers. This objective was fully achieved, as evidenced by the following unique combination of characteristics which are outstanding in the new variety and which distinguish it from its parents, as well as from all other varieties of which I am aware:

(1) Free, vigorous and upright habits of growth;
(2) Good flower productivity;
(3) Long flower stems suitable for commercial cut flower production;
(4) A distinctive and attractive pink flower color; and
(5) Exceptionally good keeping qualities of the flowers as cut flowers.

In comparison with its seed parent "Stoplite," the new variety is a substantial improvement thereover, and bears pink instead of red flowers, while maintaining the good keeping qualities of this parent.

As compared with its pollen parent "Lovelight," the new variety is likewise an improvement, being more productive, and having a much more desirable growth habit.

The new variety is somewhat similar to the variety "Miss M'liss" (Plant Patent No. 1,888), but is a distinct improvement thereover, especially by having longer flower stems which are desirable in present day cut flower production.

Asexual reproduction of the new variety by grafting, as performed at Richmond, Indiana, and also by budding, as performed at Livermore, California, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Robert Ridgway's Color Standards and Nomenclature (hereinafter abbreviated as (R)), Robert S. Wilson's Horticultural Colour Chart (hereinafter abbreviated as (W)), and Nickerson Color Fan (hereinafter abbreviated ae (N)), as indicated, except where general color terms of ordinary dictionary significance are obvious:

Type: Seedling; greenhouse; for cut flowers.
Class: Floribunda.
Breeding: Seedling.
*Seed parent.*—"Stoplite."
*Pollen parent.*—"Lovelight."
Propagation: Holds its distinguishing characteristics through succeeding propagations by both grafting and budding.

*Flower*

Locality where grown and following observations made: Richmond, Indiana.
Flowers borne: From one to several to a stem but usually disbudded singly for market as cut flowers; in irregular clusters; on stems of medium length and medium strength.
Quantity of bloom: Free, in greenhouse.
Continuity: Continuous, in greenhouse.
Fragrance: Slight, in greenhouse. Nature—sweetbriar.
Bud:
*Peduncle.*—Medium length; from small to medium diameter; medium strength. Bark—smooth, except for many prickles having their base Ruby Red, Plate 827/2 (W), with tips of Barium Yellow, Plate 503/3 (W). Color—from moderate Yellow Green, Plate 2.5GY 5/5 (N) to strong Yellow Green, Plate 2.5GY 6/8 (N). Thorns—none. Hairs—none.
*Before calyx breaks.*—Size—medium. Form—short pointed; with a conspicuous neck; with foliaceous appendages on the surface of the bud; with slender, much cut, foliaceous parts extending beyond the tip of the bud equal to ¼ of its length. Color—shaded from Spinach Green, Plate 0960/1 (W) to strong Yellow Green, Plate 2.5GY 6/8 (N).
*As calyx breaks.*—Color (outside)—a shade darker than Neyron Rose, Plate 623 (W), with base of Naples Yellow, Plate 403/2 (W).
*As first petal opens.*—Size—medium. Form—long pointed. Color: outside—Phlox Pink, Plate 625/1 (W), with base of Naples Yellow, Plate 403/3 (W); inside—Dawn Pink, Plate 523/1 (W), with base of Naples Yellow, Plate 403/3 (W).
*Opening.*—Opens up well in greenhouse; a slight decrease in bud size during prolonged periods of high temperatures.
Bloom:
*Size (when fully open).*—Small; from 2 inches to 2¾ inches.
*Petalage.*—Double; from 25 to 35 petals; arranged regularly.
*Form.*—High-centered at first, but becoming from flat to slightly cupped; petals being at first very tightly rolled inward, but later becoming loosely rolled inward at maturity.
Petals:
*Texture.*—Moderately thin.
*Appearance.*—Inside—satiny. Outside—velvety.
*Shape.*—Outer—oval, with width broader than length, and with apex generally flat but some having from one to several notches. Intermediate—oval, with apex slightly reniform. Inner—oval, with apex flat.

This description of a newly opened flower was made from a rose grown in a greenhouse during the month of May at Richmond, Indiana.

*Color.*—Outer petal: outside surface—shaded from Rose Bengal, Plate 25/2 (W) to Camellia Rose, Plate 622/2 (W), with base of Naples Yellow, Plate 403/3 (W); inside surface—shaded from Rose Pink, Plate 427/2 (W) to Camellia Rose, Plate 622/2 (W), with base of Naples Yellow, Plate 403/3 (W). Intermediate petal: outside surface—shaded from Rose Bengal, Plate 25/2 (W) to Neyron Rose, Plate 623/2 (W), with base of Naples Yellow, Plate 403/3 (W); inside surface—shaded from Neyron Rose, Plate 623/3 (W) to Neyron Rose, Plate 623/2 (W), with base of Naples Yellow, Plate 403/3 (W). Inner petal: outside surface—Neyron Rose, Plate 623 (W), with base of Naples Yellow, Plate 403/3 (W); inside surface—Spinel Pink, Plate 0625/1 (W), with base of Naples Yellow, Plate 403/2 (W).

This description was made from a rose that was open for three days in a greenhouse during the month of April at Richmond, Indiana.

*Color.*—Outer petal: outside surface—Rose Bengal, Plate 25/3 (W) with venation and base of Naples Yellow, Plate 403/3 (W); inside surface—Pale Pink, Plate 2.5R 9/3 (N), with base of Naples Yellow, Plate 403/3 (W). Intermediate petal: outside surface—Phlox Pink, Plate 625/1 (W), with base of Primrose Yellow, Plate 601/3 (W); inside surface—Dawn Pink, Plate 523/2 (W), with base of Naples Yellow, Plate 403/3 (W). Inner petal: outside surface—Phlox Pink, Plate 625/2 (W), with venation and base of Naples Yellow, Plate 403/3 (W); inside surface—Dawn Pink, Plate 523/2 (W), with base of Naples Yellow, Plate 403/3 (W).

*General color effect.*—Newly opened flower—Pale Pink, Plate 2.5R 9/3 (N). Three days open—a shade lighter than Carmine Rose, Plate 621/3 (W).

*Behavior.*—Petals persist in greenhouse; a slight decrease in flower and petal size during hot weather; fading to French Rose, Plate 520/3 (W).

*Flower longevity.*—Cut flowers grown in greenhouse and kept at living room temperatures—7 days in April.

*Plant*

Foliage:

*Leaves.*—Compound of 3–7 leaflets; normal abundance; medium size; moderately heavy.

*Leaflets.*—Shape—from oval to elliptical. Apex—cuspidate. Base—from obtuse to occasionally oblique. Margin—simply serrate.

*Color.*—Mature: upper surface—a shade darker than Parsley Green, Plate 00962 (W), but not as dark as Ivy Green, Plate 1060/3 (W); under surface—a shade darker than Lavender Green, Plate 000761 (W). Young: upper surface—a shade lighter than Parsley Green, Plate 00962/2 (W), with margins and some suffusion of Dark Red, Plate 5R 3/7 (N); under surface—Lavender Green, Plate 000761 (W), with edges Dark Red, Plate 5R 3/7 (N).

*Rachis (the supporting stem of the compound leaf).*—Medium. Upper side—grooved; almost smooth; with a few minute prickles. Under side—smooth; with 2 or 3 small thorns.

*Stipules.*—Short; narrow; with short points turning out at an angle of less than 90°.

Growth (in greenhouse):

*Habit.*—Upright; much-branched.

*Growth.*—Free; vigorous.

*Canes.*—Medium diameter.

*Main stems.*—Color—from slightly lighter than Spinach Green, Plate 0960/3 (W) to Spinach Green, Plate 0960/3 (W), with streaks on very old main canes from Strong Brown, Plate 5YR 4/5 (N), to Moderate Brown, Plate 5YR 3/3 (N). Thorns—several; short; from straight to slightly hooked downward; with short, narrow base; color—Strong Brown, Plate 5YR 4/5 (N), shaded to Moderate Brown, Plate 5YR 3/3 (N) on some tips and bases. Prickles—none. Hairs—none.

*Branches.*—Color—varies from Spinach Green, Plate 0960/1 (W) to Spinach Green, Plate 0960 (W). Thorns—several; short; straight; with narrow base; color—Moderate Brown, Plate 7.5YR 4/5 (N), with tips shaded as light as Brownish Orange, Plate 5YR 5/8 (N). Prickles—none. Hairs—none.

*New shoots.*—Color—varies from Strong Yellow Green, Plate 2.5GY 6/8 (N) to Moderate Yellow Green, Plate 2.5GY 5/5 (N). Thorns—several; short; straight; with narrow base; color—Ruby Red, Plate 827 (W). Prickles—none. Hairs—none.

*Reproductive Organs*

Stamens: Medium number; arranged irregularly about pistils; tucked in calyx.

Filaments: Short; most with anthers. Color—Uranium Green, Plate 63/2 (W).

Anthers: From medium size to small; open at various times. Color—Majolica Yellow, Plate 09/1 (W).

Pollen: Moderate quantity. Color—Saffron Yellow, Plate 7/1 (W).

Pistils: Medium number.

Styles: Even; medium length; medium heavy; bunched; columnar. Color—Naples Yellow, Plate 403/2 (W).

Stigma: Color—Uranium Green, Plate 63/3 (W).

I claim:

A new and distinct variety of rose plant of the floribunda class, substantially as herein shown and described, characterized particularly as to novelty by the unique combination of free, vigorous and upright habits of growth, good flower productivity, long flower stems suitable for commercial cut flower production, a distinctive and attractive pink flower color, and exceptionally good keeping qualities of the flowers as cut flowers.

No references cited.